(12) United States Patent
Neumann

(10) Patent No.: US 7,597,476 B2
(45) Date of Patent: Oct. 6, 2009

(54) APPARATUS AND METHOD FOR DETERMINING AIR-KERMA RATE

(75) Inventor: Jürgen Neumann, Germering (DE)

(73) Assignee: Dornier MedTech Systems GmbH, Wessling (DE)

( * ) Notice: Subject to any disclaimer, the term of this patent is extended or adjusted under 35 U.S.C. 154(b) by 84 days.

(21) Appl. No.: 11/936,183

(22) Filed: Nov. 7, 2007

(65) Prior Publication Data
US 2009/0119028 A1  May 7, 2009

(51) Int. Cl.
*G01D 18/00* (2006.01)
(52) U.S. Cl. ................................. 378/207
(58) Field of Classification Search ............ 378/207
See application file for complete search history.

(56) References Cited

U.S. PATENT DOCUMENTS

| 4,297,638 | A | 10/1981 | LaFrance |
| 4,386,320 | A | 5/1983 | Lafrance |
| 4,768,216 | A | 8/1988 | Harver et al. |
| 4,872,193 | A * | 10/1989 | Elff et al. ............... 378/196 |
| 5,166,969 | A | 11/1992 | Heidsieck |
| 6,292,537 | B1 * | 9/2001 | Zimmermann ........... 378/97 |
| 6,422,751 | B1 * | 7/2002 | Aufrichtig et al. ....... 378/207 |

FOREIGN PATENT DOCUMENTS

| EP | 0 979 027 A2 | 2/2000 |
| GB | 908604 | 10/1962 |
| GB | 2007950 A | 5/1979 |

OTHER PUBLICATIONS

Podgorsak et al., "Superficial and orthovoltage x-ray beam dosimetry," Medical Physics, vol. 25, Issue 7, (Jul. 1998), pp. 1206-1211.*

* cited by examiner

*Primary Examiner*—Chih-Cheng G Kao
(74) *Attorney, Agent, or Firm*—King & Spalding LLP

(57) ABSTRACT

An apparatus for determining the air-kerma rate of an x-ray device comprises a data obtaining component for obtaining data of the x-ray device, a calculation component for calculating the air-kerma rate from the obtained data, and an outputting component for outputting the calculated air-kerma rate, where the calculation component uses an algebraic formula for the calculation of the air-kerma rate.

33 Claims, 1 Drawing Sheet

APPARATUS AND METHOD FOR DETERMINING AIR-KERMA RATE

TECHNICAL FIELD

The invention generally relates to an apparatus and a method for determining the air-kerma rate of an x-ray device.

BACKGROUND

Air-kerma is expressed in units of Gray and is known as the absorbed x-ray dose in air. Kerma is the abbreviation of kinetic energy released in the medium and refers to the amount of energy of an x-ray beam absorbed per unit mass.

In conventional systems for measuring air-kerma rate, a neural network can be used to predict an air-kerma area product for a radiographic x-ray exposure. The neural network is combined with an output scaling, which leads to a very complicated device.

In another conventional system, the air-kerma (rate) can be directly measured with an ion chamber. Such measurements, however, attenuate the x-ray beam and also give rise to additional failure sources of the device.

Accordingly, a need exists in the art for an apparatus and a method for an accurate, easy, and failure-safe determination of the air-kerma rate.

DETAILED DESCRIPTION OF EXEMPLARY EMBODIMENTS

Figure 1:
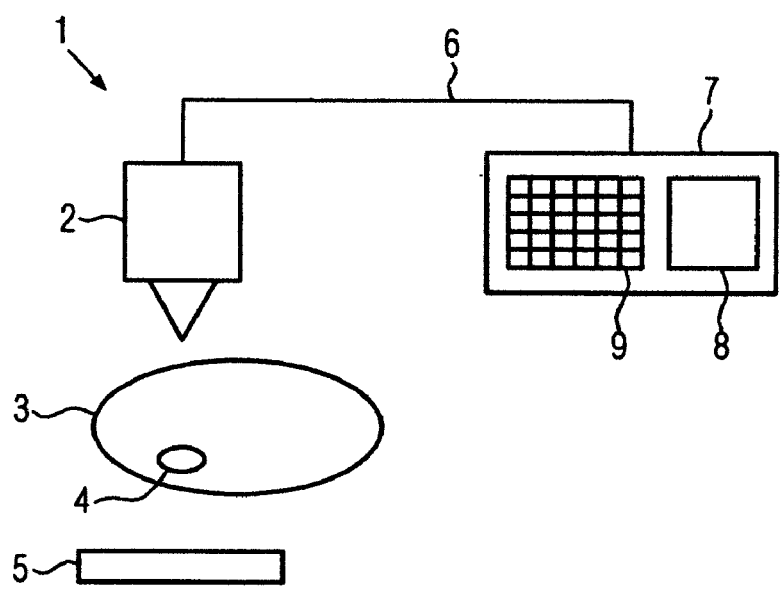
FIG. 1 is a block diagram depicting an x-ray device according to an exemplary embodiment.

According to an exemplary embodiment of the present invention, the air-kerma rate is calculated using an algebraic formula. This algebraic formula directly gives the value of the air-kerma rate. The formula has certain input variables, such as, for example, the current and the voltage of an x-ray tube. These values can be changed for each application or use of the x-ray tube and are therefore obtained for each calculation. The values of these variables may be measured with dedicated components or, alternatively, may be obtained from set values that are indicating the desired voltage or current.

The calculated air-kerma rate can be output and/or can be used internally to calculate further items. Also, a comparison of the calculated air-kerma rate to threshold values is possible. The result of the comparison can be output or can be used for further calculations or analysis. Corresponding outputting of the air-kerma rate, carrying out the further calculations and/or analysis, and/or the comparison and/or outputting any result of any further calculation, analysis, and/or comparison may be provided.

The algebraic formula can comprise one, two, three, four, or more parameters which may be calibrated once and afterwards can be used for multiple calculations of the air-kerma rate.

For using the parameters in more than one calculation, a storage medium may be provided wherein the parameters may be stored.

If variable data are obtained from set values, then separate measuring components are not needed to determine the air-kerma rate, which allows for a highly failure safe determination.

Further, the value of one variable may be measured and the value of another variable may be obtained from a set value. For example, the current I of the x-ray tube can be measured, and the voltage U can be obtained from a set value or vice versa. In an exemplary embodiment, a table of applicable x-ray tube voltages (U) and the corresponding air-kerma rates AKR can be developed. The voltages can be pre-selected, and the tube currents (I) and the air-kerma rates AKR can be measured using conventional methods at a certain point of interest.

The following algebraic formula (equation (1)) can be used to determine the air-kerma rate AKR according to an exemplary embodiment:

$$AKR = \beta * U^{\alpha} * I + \gamma \quad (1)$$

where U is an x-ray tube voltage, I is the x-ray tube current, and $\alpha$, $\beta$, and $\gamma$ are calibration parameters. A linear relationship between $U^{\alpha}*I$ and the measured AKR can be obtained by varying the parameter alpha. In an exemplary embodiment, the coefficients beta and gamma can be determined by means of a Least Square Method to obtain the best approximation for a linear result of the equation (1). Other algebraic formulas also are suitable. For example, $U^{\alpha}*I$ may be substituted by $U*I^{\alpha}$ and $\beta$ and $\gamma$ may be substituted by $\beta'$, $\gamma'$.

Furthermore, in some cases, the following algebraic formula (equation (2)) can be used to determine the air-kerma rate AKR according to another exemplary embodiment and may provide better accuracy compared to the accuracy of equation (1):

$$AKR = (\beta * U^{\alpha*} + \gamma)*I + \delta \quad (2)$$

Instead of three calibration parameters as used in equation (1), equation (2) uses four calibration parameters (with the addition of $\delta$). In exemplary embodiments, the additional parameters are empirical values to achieve individual approximations in special cases, for example, for very small exposure times or if the parameter gamma depends on the current. As shown in equation (2), the independent gamma $\gamma$ was substituted by $\gamma*I+\delta$.

From the air-kerma rate AKR, the dose (air-kerma AK) can be obtained with the following formula (equation (3)) according to an exemplary embodiment:

$$AK = AKR*t \quad (3)$$

where AKR is the air-kerma rate calculated using equation (1) or (2), and t is the irradiation time.

The following formula (equation 4)) also can be used to calculate the air-kerma AK according to another alternative exemplary embodiment and is particularly useful for irradiation times less than 5, 10, 15, or 20 milliseconds:

$$AK = AKR*t/(1+\epsilon*\exp(-\tau*t)) \quad (4)$$

The parameters $\epsilon$ and $\tau$ in equation (4) are additional parameters which may be obtained from suitable calibration procedures. Also in equation (4), AKR is the air-kerma rate calculated using equation (1) or (2), and t is the irradiation time.

Figure 2:
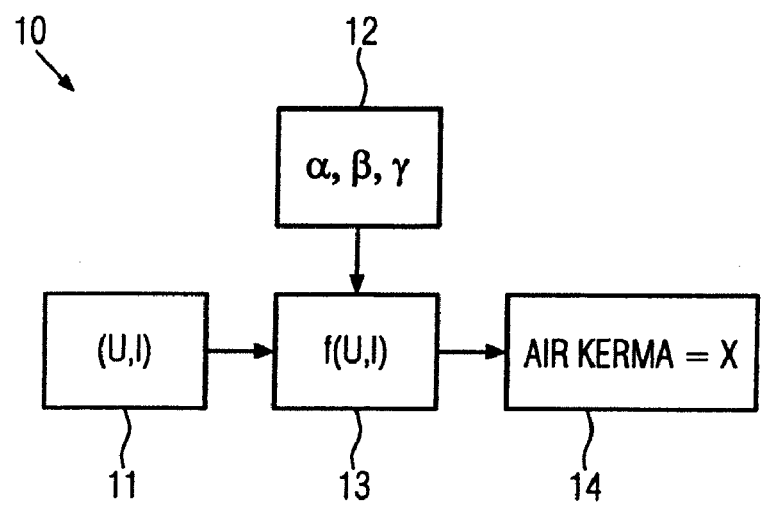
FIG. 2 is a schematic diagram depicting an apparatus for determining the air-kerma rate of the x-ray device illustrated in FIG. 1 according to an exemplary embodiment.

With reference to FIGS. 1 and 2, exemplary embodiments of the invention will be described. FIG. 1 is a block diagram depicting an x-ray device 1 according to an exemplary embodiment. FIG. 2 is a schematic diagram depicting an apparatus 10 for determining the air-kerma rate of the x-ray device 1 illustrated in FIG. 1 according to an exemplary embodiment.

In FIG. 1, a diagnostic x-ray device 1 is shown. An x-ray tube 2 emits x-rays, which are transmitted through a body 3 of a patient where an item 4 is to be investigated. Further, a sensing device 5 receives the transmitted x-ray radiation to form an image.

The device 1 may be part of, for example, a lithotripter where the x-ray device 1 is used to locate concrements, such as kidney stones or the like.

The x-ray tube 2 has a connection 6 to a control device 7. The control device 7 has input devices 9 and output devices 8. Via the input device 9, for example, a tube current or a tube voltage may be set. These set values are applied to the x-ray tube 2.

In the control device 7, the air-kerma rate (see equation (1) or (2)) may be calculated and output on the display 8 together with other information or alone. On the display 8, the calculated air-kerma (see equation (3) and (4)) may additionally or alternatively be output.

In FIG. 2, an apparatus 10 for determining the air-kerma rate is shown. This apparatus 10 may be included in the control device 7 shown in FIG. 1.

In FIG. 2, a data obtaining component 11 obtains data regarding the operation of the x-ray device 1. Here, the tube current I and the tube voltage U are obtained, where these obtained values may be set values entered via the input devices 9 or measured values during the operation of the x-ray device 1. Furthermore, a storage medium 12 stores calibration parameters alpha $\alpha$, beta $\beta$, and gamma $\gamma$. Although not illustrated in FIG. 2, the storage medium 12 also can store calibration parameters delta $\delta$, epsilon $\epsilon$, and tau $\tau$. These calibration parameters may be stored once in the storage medium 12 and then may be read multiple times for different calculations.

The calculation component 13 reads the parameters $\alpha$, beta $\beta$, and gamma $\gamma$, and optionally reads the parameters delta $\delta$, epsilon $\epsilon$, and tau $\tau$, from the storage medium 12, receives the data (tube voltage U and tube current I) from the data obtaining component 11, and evaluates the data and parameters by use of an algebraic formula f. With this formula f, the air-kerma rate is determined and output by an outputting component 14. In exemplary embodiments, the formula f can be equation (1) or (2). Further, the air-kerma may be calculated using equation (3) or (4) and output in component 14. This outputting component 14 may, for example, be given by the display 8 in FIG. 1.

In an exemplary embodiment, to obtain in a calibration procedure the parameters alpha $\alpha$, beta $\beta$, gamma $\gamma$, delta $\delta$, epsilon $\epsilon$, and tau $\tau$ for storage in the storage medium 12, the x-ray tube 2 is operated at different currents I and different voltages U. The air-kerma rate is measured during this calibration procedure for the different set values of I and U or for measured values of I and U.

The exponent alpha $\alpha$ is determined such that the product of $U^{\alpha}*I$ gives a linear ($\gamma=0$) or affine ($\gamma \neq 0$) relation with the air-kerma rate. Alternatively, equation (2) may be used.

The values of alpha $\alpha$, beta $\beta$, gamma $\gamma$ (and optionally delta $\delta$, epsilon $\epsilon$, and tau $\tau$) are then used for the calculation of the air-kerma rate and/or the air-kerma. Also, for values of U and I for which previous measurement was not performed during the calibration, the values for the air-kerma rate can be interpolated for such values of U and I.

The obtained values (in other words, the values which are not calibration parameters) can be obtained for each calculation. Further, on every change of one of the values (in particular of the voltage U and/or the current I) the calculation can be repeated. The calculation can be performed repeatedly, such as, for example, each 10 milliseconds or only upon a detected change in one of the input values (U and/or I).

Although the exemplary embodiment described with reference to FIG. 1 is a diagnostic x-ray device 1, the device 1 may be a diagnostic x-ray device, a therapeutic x-ray device, or another suitable type of x-ray device.

In an exemplary embodiment, the components 11, 13, and 14 can comprise one or more software modules executing on a processor.

The invention claimed is:

1. An apparatus for determining the air-kerma rate of an x-ray device, comprising:
    a data obtaining component for obtaining data for the x-ray device; and
    a calculation component for calculating the air-kerma rate from the obtained data,
    wherein the calculation component uses an algebraic formula to calculate the air-kerma rate,
    wherein the algebraic formula for the air-kerma rate is:

$$\text{air-kerma rate}=\beta*U\alpha*I+\gamma,$$

wherein U is an operating voltage of an x-ray tube of the x-ray device, I is an operating current of the x-ray tube of the x-ray device, and $\alpha$, $\beta$, and $\gamma$ are calibration parameters.

2. The apparatus according to claim 1, further comprising a storage medium that receives and stores the calibration parameters,
    wherein the calculation component reads the calibration parameters from the storage medium.

3. The apparatus according to claim 1, further comprising a control device that sets values of the data for operation of the x-ray device,
    wherein the data obtaining component obtains the data from the control device.

4. The apparatus according to claim 1, wherein the data obtaining component obtains the data from measurements of values used to operate the x-ray device.

5. The apparatus according to claim 1, wherein the data comprises the voltage U and the current I of the x-ray tube of the x-ray device.

6. The apparatus according to claim 1, wherein the calculation component further calculates an air-kerma (AK) based on the calculated air-kerma rate (AKR), using one of the formulas $$AK=AKR*t \text{ or } AK=AKR*t/(1+\epsilon*\exp(-\tau*t)),$$

wherein t is the irradiation time, and wherein $\epsilon$ and $\tau$ are calibration parameters.

7. The apparatus according to claim 1, wherein the apparatus is a diagnostic x-ray device.

8. The apparatus according to claim 1, wherein the apparatus is a lithotripter.

9. A method for determining the air-kerma rate of an x-ray device, comprising the steps of:
    obtaining data of the operation of the x-ray device; and
    calculating via a calculation component the air-kerma rate from the obtained data,
    wherein the calculating step uses an algebraic formula to calculate the air-kerma rate,
    wherein the algebraic formula for the air-kerma rate is:

$$\text{air-kerma rate}=\beta*U\alpha*I+\gamma,$$

wherein U is an operating voltage of an x-ray tube of the x-ray device, I is an operating current of the x-ray tube of the x-ray device, and $\alpha$, $\beta$, and $\gamma$ are calibration parameters.

10. The method of claim 9, further comprising the steps of calibrating and storing the calibration parameters used in the algebraic formula.

11. The method of claim 9, wherein the step of obtaining data comprises obtaining set values of the data for the operation of the x-ray device.

12. The method of claim 9, wherein the step of obtaining data comprises obtaining measured values of the data for the operation of the x-ray device.

13. The method of claim 9, wherein the data comprises the voltage U and the current I of the x-ray tube of the x-ray device.

14. The method of claim 9, wherein the calculation step further comprises calculating via the calculation component an air-kerma (AK) based on the calculated air-kerma rate (AKR), using one of the formulas $$AK=AKR*t \text{ or } AK=AKR*t/(1+\epsilon*\exp(-\tau*t)),$$

wherein t is the irradiation time, and wherein $\epsilon$ and $\tau$ are calibration parameters.

15. The method of claim 9, wherein the method is performed in a diagnostic x-ray device.

16. The method of claim 9, wherein the method is performed in a lithotripter.

17. An apparatus for determining the air-kerma rate of an x-ray device, comprising:
a data obtaining component for obtaining data for the x-ray device; and
a calculation component for calculating the air-kerma rate from the obtained data,
wherein the calculation component uses an algebraic formula to calculate the air-kerma rate,
wherein the calculation component further calculates an air-kerma (AK) based on the calculated air-kerma rate (AKR), using one of the formulas $$AK=AKR*t \text{ or } AK=AKR*t/(1+\epsilon*\exp(-\tau*t)),$$

wherein t is the irradiation time, and wherein $\epsilon$ and $\tau$ are calibration parameters.

18. The apparatus according to claim 17, wherein the algebraic formula comprises at least one parameter that can be calibrated to calculate the air-kerma rate.

19. The apparatus according to claim 18, further comprising a storage medium that receives and stores the at least one parameter,
wherein the calculation component reads the at least one parameter from the storage medium.

20. The apparatus according to claim 17, further comprising a control device that sets values of the data for operation of the x-ray device,
wherein the data obtaining component obtains the data from the control device.

21. The apparatus according to claim 17, wherein the data obtaining component obtains the data from measurements of values used to operate the x-ray device.

22. The apparatus according to claim 17, wherein the data comprises a voltage and a current of an x-ray tube of the x-ray device.

23. The apparatus according to claim 17, wherein the algebraic formula for the air-kerma rate is:

$$\text{air-kerma rate}=\beta*U\alpha*I+\gamma,$$

wherein U is an operating voltage of an x-ray tube of the x-ray device, I is an operating current of the x-ray tube of the x-ray device, and $\alpha$, $\beta$, and $\gamma$ calibration parameters.

24. The apparatus according to claim 17, wherein the apparatus is a diagnostic x-ray device.

25. The apparatus according to claim 17, wherein the apparatus is a lithotripter.

26. A method for determining the air-kerma rate of an x-ray device, comprising the steps of:
obtaining data of the operation of the x-ray device; and
calculating via a calculation component the air-kerma rate from the obtained data,
wherein the calculating step uses an algebraic formula to calculate the air-kerma rate,
wherein the calculation step further comprises calculating via the calculation component an air-kerma (AK) based on the calculated air-kerma rate (AKR), using one of the formulas $$AK=AKR*t \text{ or } AK=AKR*t/(1+\epsilon*\exp(-\tau*t)),$$

wherein t is the irradiation time, and wherein $\epsilon$ and $\tau$ are calibration parameters.

27. The method of claim 26, further comprising the steps of calibrating and storing parameters used in the algebraic formula.

28. The method of claim 26, wherein the step of obtaining data comprises obtaining set values of the data for the operation of the x-ray device.

29. The method of claim 26, wherein the step of obtaining data comprises obtaining measured values of the data for the operation of the x-ray device.

30. The method of claim 26, wherein the data comprises a voltage and a current of an x-ray tube of the x-ray device.

31. The method of claim 26, wherein the algebraic formula for the air-kerma rate is:

$$\text{air-kerma rate}=\beta*U\alpha*I+\gamma,$$

wherein U is an operating voltage of an x-ray tube of the x-ray device, I is an operating current of the x-ray tube of the x-ray device, and $\alpha$, $\beta$, and $\gamma$ are calibration parameters.

32. The method of claim 26, wherein the method is performed by a diagnostic x-ray device.

33. The method of claim 26, wherein the method is performed by a lithotripter.

* * * * *